(12) United States Patent
Misra

(10) Patent No.: US 6,541,222 B1
(45) Date of Patent: Apr. 1, 2003

(54) PLANT PROMOTER ISOLATED FROM DOUGLAS-FIR 2S SEED STORAGE PROTEIN GENE

(75) Inventor: Santosh Misra, Victoria (CA)

(73) Assignee: University of Victoria Innovation and Development Corporation, Victoria (CA)

( * ) Notice: Subject to any disclaimer, the term of this patent is extended or adjusted under 35 U.S.C. 154(b) by 0 days.

(21) Appl. No.: 09/627,536

(22) Filed: Jul. 28, 2000

(51) Int. Cl.[7] .................... C12P 21/06; C12N 15/00; C12N 5/04
(52) U.S. Cl. .................. 435/69.1; 435/320.1; 435/419
(58) Field of Search ........................ 435/320.1, 419, 435/69.1, 6; 800/295, 287; 536/23.1, 24.1

(56) References Cited

U.S. PATENT DOCUMENTS 5,589,615 A   12/1996  De Clercq et al.
5,804,558 A  *  9/1998  Lehrer et al.

OTHER PUBLICATIONS

Grant et al. Characterization of the Rat Hippocalcin Gene The 5' Flanking Region directs expression to the Hippocampus. (1996), Neuroscience, vol. 75, No. 4, pp. 1099–1115.*

Chatthai et al., "Sequence and Expression of Embryogenesis–Specific cDNAs Encoding 2S Seed Storage Proteins in *Pseudotsuga Menziesii* [Mirb.] Franco," *Planta* 206:138–145 (1998).

Chatthai, "Molecular Characterization and Regulation of Embryogenesis–Associated Genes in Douglas–Fir (*Psuedotsuga Menziesii* [MIRB.] Franco)," pp. 1–84, 1999.

* cited by examiner

*Primary Examiner*—Sean McGarry
*Assistant Examiner*—Janet Epps
(74) *Attorney, Agent, or Firm*—Klarquist Sparkman, LLP

(57) ABSTRACT

The invention provides a Douglas-fir 2S seed-storage promoter (df2SSP; SEQ ID NO: 17) and methods of its use. The promoter is useful for, among other things, directing the tissue-specific expression of transgenes.

29 Claims, 2 Drawing Sheets

```
                                              I                              IV              -1014
Pm  gaattcgtactctgctttgtatcgagttattgtgttttttgttttacacgtggcagggatcttgtttgttatttctatgcacttagtcactactgtaattt
              I                                                                                -914
Pm  ggttaagaattttaattcagatgcagttaaagatgaagagcatatctagttgaaaaactatgagcttaactagcttcggaggcagagctaaagtagttag
                                                                                               -814
Pm  gacagaagtaaaaacatcataaatagaaatagagcatgtagctttgttagatctaacatcaaaaccataaacaacagggttagtttaccttatttctcaa
      I                                                                                        -714
Pm  gtgcaaaggcaggaacatatccataggttccagatgcatagtttggagcagtggttccagatttcgacaaagcatatctacatcctatagattaagttga
                                  I                                                            -614
Pm  actggcaacataagtgacagcatatctacatctggtaggctatggcatcaacggtggtgtgtcttatcaagggtcatccaccttgtgaaagggtgtgaca
        IV              IV     IV                                                              -514
Pm  tgcattaacaaagtcctaccatcaaattgtgaaatgcattatgcatcagataggtggcaccatcatgtttcaagtaagtaagatagtgttgtgaagtggt
                                III                                                            -414
Pm  gattccctcataccagactagaaaaattaatatttaatgttaatattaatgttagcattattgaacttcataatctcttagtgaactaagtgggttatgt
                IV                                                 IV                          -314
Pm  ctgggttatttcttgagattacgtcgttcccaatagaagtgttgttgcgttaaaccttgccgatgaaacaacgtgaaacatctacaccaccttacgaaa
                           V                             IV                              IV
Pm  aatggcattacgagaagaggaaggcagtttatcatcaactaattagtttgtctaaatgcaataagcctaagtagtgttgttgagacgctagactgcactg
Pg                                       ..c..c.....c...------------
                    I                            ......................                       -131
Pm  tcgcggattccacatgcccg----caagattc-ctctaatc---gaaagacgcggcgattggaaatagaggt----aggctttctttctcag-----gga
Pg  .a-...cc------......ctaa.........gtcttt............c.......c..t..cagcc....g...c....a.t.gcttt..
        IV                  II         I                   V                                   -38
Pm  cgtggaatccgaattggggcatgctttacatgtgttcgt---ttcgtcatcgtc----tgtattctacgtccctacagcatacagacaccttcaattccc
Pg  ......gagt..gac.ct......accg........cacgc...tctg.....gtgt...g...gt....ggaaga-------.......a....ct....t
                                                    +1                                         48
Pm  ggg----cttttataaata-----------cccacttactcttcccaacttcacactcgcgcttcatctatcaatccatcattcattgtaacgaagaaag
Pg  ctcccag.c..c.taaatacaacaata.........gt...c....c.....g....t..at.a.g.tc....cggg.ag.aagga-------.......
                                                                                                148
           M  G  V  F  S  P  S  T  T  K  L  T  L  K  W  L  S  V  G  V  A  L  L  L  L  H  W
Pm  aacagcgaaagagcaATGGGTGTTTTTTCCCCTTCGACAACGAAGCTGACGCTTAAATGGCTGAGTGTAGGCGTGGCGCTTCTCCTTCTCCTTCACTGGG
Pg  ...a.agctg.a............C.........G.....C......T.C...T..TC...C..C..GT...C............
                                             .     .     R  .  .  .  F  .  L  S  .     .  F  .  .  .  .
                                                                                                236
     G  T  P  D  V  D  A  H  E  H  N  I  Y  G  E  N  S  Q  Q  Q  Q  Q  R  R  G  S  C  D  P  -  -  -  -  E
Pm  GTACCCCGACGTTGACGCGCATGAACACAATATATATGGAGAAAATTCGCAACAGCAACAGCAACGACGCGGGTCGTGCGATCCG------------GA
Pg  ...TT...AGT.....TGGC......G.........G........GG.GATA.....A...AGA---------C..........C..TCAGAGACACCCGC.
     .  I  .  S  .  .  G  .  .  D  .  M  .  .  E  I  .  .  R  -  -  -  R  .  .  .  Q  R  H  P  Q
                                                                                                336
     R  L  S  S  C  R  D  Y  L  E  R  R  R  E  Q  P  S  E  S  C  C  N  E  L  E  R  M  S  P  Q  C  R  C
Pm  GAGATTGTCTTCTTGCCGGGACTACTTGGAGCGGCGGAGAGAGCAGCCATCGGAGAGTTGCTGCAACGAATTGGAAAGAATGTCTCCACAATGCCGATGC
Pg  ............A..............C..........................R......G.G.......C...............
     .  .  .  .  .  .  .  .  .  .  .  .  .  .  .  .  .  R  .  E  .  Q  .  .  .  .  .  .  .  .  .  .  .
                                                                                                414
     P  A  I  Q  Q  V  L  D  Q  S  -  -  -  A  S  T  F  M  D  S  D  -  -  -  D  A  -  L  N  Q  R  R  G
Pm  CCAGCCATACAGCAAGTGCTCGATCAATCT---------GCATCGACCTTCATGGATTCTGAC---------GATGCA---CTTAATCAACGCCGTGGG-
Pg  .A...G.........A...........TTATCGTAT---GATT................TCTCAGGAG...A..CCA..........A..CC.CC
     Q  .  .  .  .  M  .  .  .  .  L  S  Y  -  D  S  .  .  .  .  S  Q  E  .  T  P  .  .  .  .  .  R
                                                                                                509
     -  -  P  R  R  A  G  R  R  E  E  Q  E  M  A  E  R  A  R  Y  L  P  D  T  C  N  V  Q  E  P  P  R  R  C
Pm  -----CCGCGAAGGGCAGGTCGAAGAGAAGAGCAGGAGATGGCGGAGAGAGCCCGATACCTTCCAGATACATGCAACGTCCAGGAGCCTCCCCGCCGCTG
Pg  GCCGC.GCGA.G...CGC..AA..GAC..G...G...T....---......AGC.........GA....C......T.GC.....C.........
     R  R  R  E  G  R  .  .  D  .  .  E  V  .  -  -  .  .  A  .  .  N  .  .  .  R  .  .  .  .  .
```

D  I  R  R  P  S                                                                              609
Pm  CGATATTCGACGCCCCTCTCgtaagtctctcccagttactaattaatagaatatcgcccctctcgtaagtctctcccagttactaattaatagacaaata
Pg  ........A.....A.........ct..---------...c---------.......................c.....t---...gt..c
     .  .  Q  .  H  .
                                                                                                709
Pm  gtaactaatttgggtagctgttttagtagggagctgcggtccagcgttttaagtatgatgtggttaagcacattatttcatgttaatgctatctatttta
Pg  a....t..-------..ga.-----------.aa..---......t.-.a.c..-...a.c...c...t.....a.a.-......-.c.g.ca.g.t.c.g...
                                                                                                809
Pm  atacattctatagtccaccattttcgttgacataattt acatatatgtaagcacttcccttgcctgccataatgaatgatgaaattaatttatgtactgg
Pg  -----...c....cc.....--......--aa....t-.........ag.----------..t..----------------------g..gt.....c-.g....
           R  Y  S  I  R  G  V  S  F  *                                                        909
Pm  ttgtgggtgtacagGCTATTCCATAAGGGGCGTCAGTTTTTGAgtgacgaacaagaagagaatatagatactatgtagataaataaacgaggggagcact
Pg  .-..c--..g..........T...G.C....AG.......AAGTGAt...cg.........a...........gc..g------..tg.t.t.tat.tc.c
           .  .  F  M  T  .  S  .  .  K  *
                                                                                                1009
Pm  tcaaaccgctatgaatttgtggttttcgttttcgttttggaggagcttattatagttatatatctataggctctcatctaatttcatttgacgcccagcg
Pg  .a..taa---..a.-----------------g.....ca..acc----.c....g....t.t.-..t.tctgc----...t..-a..ta-tagc.t
                                                                                                1109
Pm  cttgtatcatagccggatctattccctggtatgtaataaagaactgaatgaatgagaaaattgatttcatggtaggatctcttttcttcttttcttcggt
Pg  ..ca.tca..gctcacca..t...a..tac..catg
                                                                                                1209
Pm  ttcatctaatgggcgccacttacttcatagcaggaccacttctcttatatgtaataaagcaataaagcactgaatgaacgagcaaactcaagtttcagag
                                                                                                1309
Pm  taaagagtagaagtagactcattaagtatcttaaaatgtccaacttcgcatacatcacaactagcagctcaaattttttgaatgattatcaattgccgagt

Figure 1

PLANT PROMOTER ISOLATED FROM DOUGLAS-FIR 2S SEED STORAGE PROTEIN GENE

FIELD

This invention relates to an isolated Douglas-fir 2S seed-storage protein promoter sequence, and methods for its use.

BACKGROUND

2S Seed-Storage Proteins

"2S" seed-storage proteins are proteins produced in seeds in a variety of different plants. Genes encoding 2S seed-storage proteins have been characterized in several plants, including Arabidopsis (Krebbers et al., *Plant Physiol.* 87:859–866, 1988; and Guerche et al., *Plant Cell* 2:469–478, 1990), canola (Baszcynski and Fallis, *Plant Mol. Biol.* 14:633–635, 1990; Jefferson et al., *EMBO J.* 6:3901–3907, 1987; and Scofield and Crouch, *J. Biol. Chem.* 262:12202–12208, 1987), radish (Raynal et al., *Gene* 99:77–86, 1991), Brazil nut (Gander et al., *Plant Mol. Biol.* 16:437–448, 1991), sunflower (Allen et al., *Mol. Gen. Genet.* 210:211–218, 1987), and rice (Adachi et al., *Plant Mol. Biol.* 21:239–248, 1993). In all of these plants, the 2S seed-storage proteins are encoded by multigene families with copy numbers in the range of 4–20. Most of the previously characterized 2S seed-storage proteins are produced from genes lacking introns; however, the BE2S1 and BE2S2 genes from Brazil nut and the HaG5 gene from sunflower contain a single intron.

The expression of storage-protein genes is restricted both spatially (to the tissues of the embryo and/or the endosperm) and temporally (to maturation and late embryogenesis) during seed development (Goldberg et al., *Cell* 56:149–160, 1989). The expression characteristics of the storage-protein genes parallel those desirable for the expression of heterologous proteins in seed. Such expressions offer the possibility of, for example, producing large quantities of easily harvested polypeptides and expressing proteins that improve grain quality. Discussions of this concept can be found in U.S. Pat. No. 5,714,474 issued to VanOoijen et al.

The strict spatial and temporal expression of genes encoding seed-storage proteins, is believed to be controlled primarily at the transcriptional level (Goldberg et al., *Cell* 56:149–160, 1989; and Stålberg et al., *Plant Mol. Biol.* 23:671–683, 1993). An increase in mRNA accumulation occurs simultaneously with an increase in transcriptional activity (DeLisle and Crouch, *Plant Physiol.* 91:617–623, 1989). Similarly, mRNA levels peak and decline as seed development proceeds, in parallel with peaks and declines in transcription levels (Gatehouse and Shirsat, *Control of Plant Gene Expression*, CRC Press, Boca Raton, Florida, pp.357–372, 1993). A number of studies have identified regulatory promoter elements associated with the expression level, developmental stage, and tissue-specific gene expression of genes for 2S seed-storage proteins (De Clercq et al., *Plant Physiol.* 92:899–907, 1990; Grossi de Sa et al., *Plant Sci.* 103:189–198, 1994; Radke et al., *Theor. Appl. Genet.* 75:685–694, 1988; and Stålberg et al., *Plant Mol. Biol.* 23:671–683, 1993).

It is generally accepted that transcriptional gene regulation depends on the interaction between promoter elements and transcription factors. For storage-protein genes, a number of nuclear factors have been identified that bind specifically to conserved cis-regulatory sequences and may activate gene transcription (Morton et al., *Regulation of Seed Storage Protein Gene Expression*, Kigel and Galili (eds.) Marcel Dekker, Inc., New York, pp. 103–138, 1995). The most studied plant-protein factors are those interacting with the G-box and related elements. Several cDNA clones encoding G-box binding factors have been isolated from a number of plant species using the G-box as a probe. These include the wheat Em-binding protein EmBP-1 (Guitinan et al., *Science* 250:267–271, 1990), G-box binding factors GBF-1, GBF-2, and GBF-3 from Arabidopsis (Schindler et al., *EMBO J.* 11:1275–1289, 1992), and tobacco TAF-1 (Oeda et al., *EMBO J.* 10:1798–1802, 1991). Most of these proteins belong to the basic leucine zipper (bZIP) family of transcription factors that are characterized by a bipartite DNA-binding domain consisting of a basic region involved in sequence-specific binding, and a leucine zipper region required for dimerization (de Vetten and Ferl, *Int. J. of Biochem.* 26:1055–1068, 1994). However, the proteins differ in their overall structure and in their binding site-preferences for the ACGT-core sequence (SEQ. ID NO: 4; Schindler et al., *Plant Cell* 4:1309–1319, 1992), the TGACG (SEQ. ID NO: 20) sequence (Schindler et al., *EMBO J.* 11:1275–1289, 1992), or the CANNTG motif (SEQ. ID NO: 1; Kawagoe and Murai, *Plant J.* 2:927–936, 1992). Some G-box binding factors can recognize deviant sequences (Foster et al., *Plant J.* 8:192–200, 1994), which allows the factors to out-compete other bZIP proteins and, in some cases, to negatively regulate gene transcription (Chem et al., *Plant Cell* 8:305–321, 1996; and Chem et al., *Plant J.* 10:135–148, 1996). Opaque2 gene products in monocotyledonous plants also contain a bZIP domain that recognizes the ACGT-core-containing DNA sequence (Schmidt et al., *Plant Cell* 4:689–700, 1992; Williams et al., *Plant Cell* 4:485–496, 1992; and Vettore et al., *Plant Mol. Biol.* 36:249–263, 1998). The gene products are notable for their role in regulation of storage-protein (zein) gene expression in maize endosperm (Unger et al., *Plant Cell* 5:831–841, 1993).

Recently, several cDNAs have been isolated from seed-specific cDNA expression libraries using cis-elements derived from genes for seed-storage proteins as probes. These cDNAs encode proteins containing bZIP, Zinc-finger, RING-finger, or basic helix-loop-helix DNA-binding domains and may represent novel types of trans-acting factors (Kawagoe and Murai, *Plant Sci.* 116:47–57, 1996; and Wohlfarth et al., *J. Plant Physiol.* 152:600–606, 1998).

SUMMARY

The invention provides a promoter for a seed-storage protein from Douglas-fir (*Pseudotsuga menziesii*). The seed-storage protein promoter (termed herein the df2SSP promoter) is capable of driving the expression of a transgene as well as the endogenous seed-storage protein gene. The promoter and variants of the promoter are useful for expressing heterologous proteins either transiently in host cells or transgenically in stably transformed cells. The df2SSP promoter (SEQ ID NO: 17) can allow for tissue-specific expression of genes that are placed under its control.

One aspect of the invention provides the df2SSP promoter (SEQ ID NO: 17), fragments/deletion mutants thereof, and variants thereof. The variant df2SSP promoters are characterized by their retention of at least 50% sequence identity with the disclosed promoter sequence (SEQ ID NO: 17), or by their retention of at least 20, 30, 40, 50, or 60 consecutive nucleic acid residues of the disclosed promoter sequence (SEQ ID NO: 17). In each case these promoters, at a minimum, retain promoter activity. In some cases these promoters retain native df2SSP promoter activity.

It is contemplated that promoters such as the CaMV 35S promoter may be altered through the introduction of sequences found in the df2SSP promoter. The resulting promoter also will be characterized by its retention of at least 20, 30, 40, 50, or 60 consecutive nucleic acid residues of the disclosed promoter sequence (SEQ ID NO: 17).

Another aspect of the invention provides vectors containing the above-described promoters and variants thereof. The vectors can be transformed into host cells. In some cases the resulting host cell can give rise to a transgenic plant.

The invention also provides transgenes. These transgenes include one of the above-described promoter sequences operably linked to one or more open reading frames (ORFs). The transgenes can be cloned into vectors and subsequently used to transform host cells, such as bacterial, insect, mammalian, fungal, yeast, or plant cells.

Accordingly, the invention also provides transgenic plants such as maize, wheat, rice, millet, tobacco, sorghum, rye, barley, brassica, sunflower, seaweeds, lemna, oat, soybean, cotton, legumes, rape/canola, alfalfa, flax, sunflower, safflower, brassica, cotton, flax, peanut, and clover; lettuce, tomato, cucurbits, cassava, potato, carrot, radish, pea, lentil, cabbage, cauliflower, broccoli, Brussels sprouts, peppers and other vegetables; citrus, apples, pears, peaches, apricots, walnuts, and other fruit trees; orchids, carnations, roses, and other flowers; cacao; poplar, elms, and other deciduous trees; pine, Douglas-fir, spruce, and other conifers; turf grasses; cacao; and rubber trees and other members of the genus Hevea.

In yet another embodiment, the invention provides methods for expressing proteins in host cells, such as plant host cells. Such methods involve operably linking a promoter, such as those described above, to at least one ORF to produce a transgene and introducing the transgene into a plant. Accordingly, the invention also provides proteins that are produced by these methods.

An alternative method for characterizing promoters includes analyzing the various promoter elements found within the promoter sequence. Hence, the invention also provides promoters that maintain promoter activity and include at least eight promoter elements selected from the group consisting of E-box motifs (SEQ ID NO: 1), RY-repeat elements (SEQ ID NO: 2), AT-rich regions (SEQ ID NO: 3), ACGT-core elements (SEQ ID NO: 4), opaque-2-like elements (SEQ ID NO: 5), and conserved gymnosperm-like regions (SEQ ID NOs: 6 and 7) and duplicates thereof, wherein the promoter displays promoter activity. The invention also provides promoters that contain all the following promoter elements in the following orientation 3'-E-box motif (SEQ ID NO: 1); ACGT-core element (SEQ ID NO: 4); E-box motif (SEQ ID NO: 1); E-box motif (SEQ ID NO: 1); E-box motif (SEQ ID NO: 1); E-box motif (SEQ ID NO: 1); ACGT-core element (SEQ ID NO: 4); ACGT-core element (SEQ ID NO: 4); ACGT-core element (SEQ ID NO: 4); AT-rich region (SEQ ID NO: 3); ACGT-core element (SEQ ID NO: 4); ACGT-core element (SEQ ID NO: 4); gymnosperm-like region (SEQ. ID NOs: 6 or 7); ACGT-core element (SEQ ID NO: 4); E-box motif (SEQ ID NO: 1); opaque-2-like element (SEQ ID NO: 5); gymnosperm-like region (SEQ. ID NOs: 6 or 7); ACGT-core element (SEQ ID NO: 4); opaque-2-like element (SEQ ID NO: 5); gymnosperm-like region (SEQ ID NOs: 6 or 7); ACGT-core element (SEQ ID NO: 4); RY-repeat element (SEQ ID NO: 2); E-box motif (SEQ ID NO: 1); and opaque-2-like element (SEQ ID NO: 5) -5'.

Finally, the invention also provides vectors, host cells, and transgenic plants that include the promoters that are described above.

These and other aspects of the invention will become readily apparent from the following detailed description.

BRIEF DESCRIPTION OF THE FIGURES

FIG. 1 shows a comparison of the nucleic acid sequence encoding the Douglas-fir 2S seed-storage protein (gPm2S1; SEQ ID NO: 10) to the white spruce Pg2S albumin gene. FIG. 1 also shows where the promoter elements are located in the endogenous Douglas-fir 2S seed-storage-protein (df2SSP) promoter. The promoter elements are identified as follows: I denotes E-box motifs; II denotes RY-repeated elements; III denotes AT-rich regions; IV denotes ACGT-core regions; V denotes opaque-2-like elements; and VI denotes gymnosperm-like regions.

SEQUENCE LISTING

Figure 2:
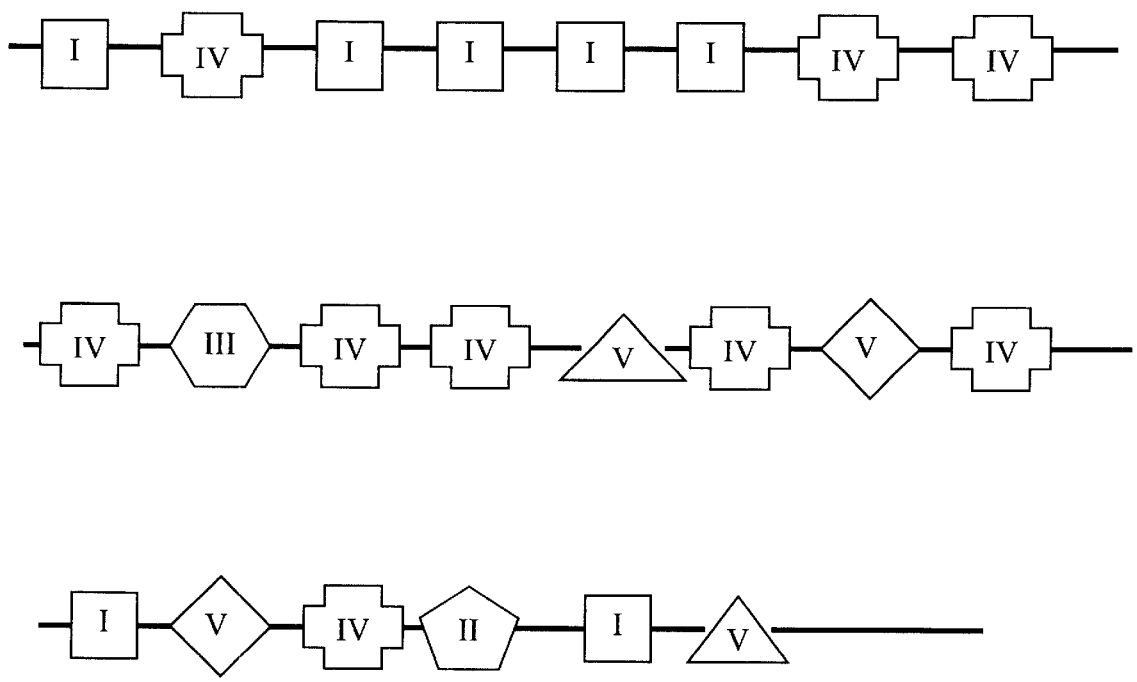
FIG. 2 is a schematic depiction of the df2SSP promoter. The promoter elements are identified as follows: I denotes E-box motifs; II denotes RY-repeated elements; III denotes AT-rich regions; IV denotes ACGT-core regions; V denotes opaque-2-like elements; and VI denotes gymnosperm-like sequences. The line that connects the elements together represents the nucleic acid strand. The regions of the line that are between the elements represent the inter-element spaces.

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleic acid sequence of an E-box motif.

SEQ ID NO: 2 is the nucleic acid sequence of a RY-repeated element.

SEQ ID NO: 3 is the nucleic acid sequence of an AT-rich region.

SEQ ID NO: 4 is the nucleic acid sequence of an ACGT-core element.

SEQ ID NO: 5 is the nucleic acid sequence of an opaque-2-like binding site.

SEQ ID NOs: 6 and 7 are the nucleic acid sequences of respective conserved "4 gymnosperm-like regions."

SEQ ID NO: 8 is the nucleic acid sequence of a TATA box.

SEQ ID NO: 9 is the nucleic acid sequence of a CAAT box.

SEQ ID NO: 10 is the nucleic acid sequence of the entire gPm2S1 gene, including the UTR and promoter.

SEQ ID NO: 11 is the nucleic acid sequence of the gPm2S1 ORF.

SEQ ID NO: 12 is the 3'-untranslated region (UTR) of the gPm2S1 gene.

SEQ ID NO: 13 is the predicted amino acid sequence of the gPm2S1 storage protein.

SEQ ID NOs: 14 and 15 are specific examples of opaque-2-like binding sites.

SEQ ID NO: 16 is a nucleic acid sequence found 5' to the initiation-start codon of the gPm2S1 gene.

SEQ ID NO: 17 is the nucleic acid sequence of the naturally occurring df2SSP promoter.

SEQ ID NO: 18 is a transcription-factor binding site.

DETAILED DESCRIPTION

I. Definitions

Unless otherwise noted, technical terms are used according to conventional usage. Definitions of common terms in molecular biology may be found in Lewin, *Genes VII*, Oxford University Press, 1999 (ISBN 0-19-879276-X); Kendrew et al. (eds.), *Encyclopedia of Molecular Biology*, Blackwell Science, Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

In order to facilitate review of the various embodiments of the invention, the following definitions are provided:

"cDNA (complementary DNA)." A "cDNA" is a piece of DNA lacking internal, non-coding segments (introns) and transcriptional regulatory sequences. cDNA may also contain untranslated regions (UTRs) that are responsible for translational control in the corresponding RNA molecule. cDNA usually is synthesized in the laboratory by reverse transcription from messenger RNA extracted from cells.

"Deletion." A "deletion" is the removal of one or more nucleic acid residues from a DNA sequence, the regions on either side of the removed sequence being joined together.

"Douglas-fir 2S seed-storage protein (df2SSP) promoter." The nucleic acid sequence of the df2SSP promoter is provided in SEQ ID NO: 17. However, the invention also encompasses variants of the df2SSP promoter that are characterized by their ability to maintain promoter activity. These variants have at least 50%, 60%, 70%, 80%, or 90% sequence identity when compared to the nucleic acid sequence shown in SEQ ID NO: 17. These variants can be isolated from nature using the hybridization or PCR techniques described below, or they can be made by manipulating the nucleic acid sequence shown in SEQ ID NO: 17.

The df2SSP promoter shown in SEQ ID NO: 17 contains several distinct promoter elements and inter-element spaces that are arranged in series in the DNA fragment. One or more of these elements or inter-element spaces can be altered, deleted, and/or duplicated without loss of promoter activity. Also, one of ordinary skill in the art will appreciate that there are other promoter elements that may be added to the promoter shown in SEQ ID NO: 17 without the loss of promoter activity and/or native df2SSP promoter activity. Hence, the invention provides promoters that maintain native promoter activity and/or promoter activity and include at least 10, 12, 14, 16, 18, 20, 22, 30, or 35 of the promoter elements contained within the df2SSP promoter (SEQ ID NO: 17).

Variants of the df2SSP promoter also can be characterized by the number of contiguous nucleic acid residues they share with the df2SSP promoter (SEQ ID NO: 17). For example, a variant of the df2SSP promoter can share at least 20, 25, 30, 40, 50, or 60 contiguous nucleic acid residues with the df2SSP promoter shown in SEQ ID NO: 17. Such variants additionally will be characterized by their ability to drive the expression of a transgene that is linked operably to it.

"Cationic Peptides." "Cationic peptides" are endogenous antimicrobial peptides produced by plants and animals typically consisting of 12–45 amino acids. Additionally, they are amphipathic molecules having a net positive charge (cationic) at physiological pH. Although cationic antimicrobial peptides (CAPs) are structurally diverse, they fall into two general classes of structures: α-helical peptides, such as the cecropins and magainans, and β-sheet peptides stabilized by intramolecular disulphide bonds, such as the defensins, protegrins, and tachyplesins. Hancock and Lehrer, *Trends Biotechnol*. 16:22–28, 1998; Zasloff, *Curr. Opin. Immunol*. 4:3–7, 1992; Cociancich et al., *Biochem. J*. 300:567–575 1994; and Piers and Hancock, *Mol. Microbiol*. 12:951–958, 1994. Natural CAPs vary greatly in their respective spectra of biological activities, including killing bacteria (Gram-positive and -negative), fungi, protozoa, and even viruses. CAPs normally kill susceptible microorganisms in vitro at concentrations from 0.25 µg/mL to 4 µg/mL (Hancock and Lehrer, *Trends Biotechnol*. 16: 22–28, 1998), providing exciting possibilities in the face of the declining efficiency of conventional antibiotics. Furthermore, the expression of CAP in plants may introduce broad-spectrum resistance to phytopathogenic microorganisms. Jaynes, *Plant Science* 89:43–53, 1993; and Misra and Zhang, *Plant Physiol*. 106: 977–981, 1994.

Cationic peptides are one type of protein that might be expressed under the control of the disclosed df2SSP promoter (SEQ ID NO:17). Other proteins that confer disease resistance, resistance to environmental stress, resistance to insect infestation, or herbicide resistance, or alter consumer-related characteristics such as shelf-life, color, or nutritional value, also may be expressed under the control of the df2SSP promoter (SEQ ID NO:17) described herein.

"Insertion." An "insertion" is the addition of a nucleotide or an amino acid residue into a nucleic acid sequence or an amino acid sequence, respectively.

"Isolated." An "isolated" biological component (such as a nucleic acid, protein, or organelle) has been substantially separated or purified away from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

"Native df2SSP Promoter Activity." "Native df2SSP promoter activity" is characterized by tissue-specific transcription and, more particularly, seed-specific transcription. The df2SSP promoter (SEQ ID NO: 17) has been shown to drive transcription in tissue from Douglas-fir seeds, such as megagametophyte tissue and tissue from zygotic embryos. Similarly, the df2SSP promoter (SEQ ID NO: 17) has been shown to drive transcription in tobacco embryos, endosperm, and cotyledons. Hence, the df2SSP promoter (SEQ ID NO: 17) shows tissue-specific activity.

Tissue-specific activity is defined as the ability of a promoter to drive a higher level of transcription in one tissue compared to transcription in another tissue. For example, the df2SSP promoter (SEQ ID NO: 17) causes a higher level of transcription in tobacco embryos than it does in tobacco leaves. Tissue-specific expression can be determined by creating transgenic plants and assaying the resulting transgenic tissues (e.g., leaves, flowers, seeds, roots) for transgene mRNA. Tissue-specific expression is quantified by comparing the level of mRNA expressed in one tissue to the level expressed in another tissue. The degree of tissue-specific expression is expressed in terms of a percentage of expression, i.e., the percentage of mRNA in one tissue compared to another. For example 100% (1×) expression reflects that an equal amount of expression is seen in two tissue types; a tissue exhibiting 200% (2×) expression is producing twice as much mRNA compared to another tissue. Native df2SSP promoter activity is, therefore, defined by the ability of the df2SSP promoter to drive expression of mRNA in seed tissues to a greater degree (i.e., at least 101%) than exhibited by the df2SSP promoter in other tissue from the same plant. Of course, the df2SSP promoter (SEQ ID NO: 17) can show an even stronger bias for expression in seed tissues, such as at least 125%, 150%, 200%, 250%, or 300% tissue-specific expression in seeds.

"Oligonucleotide ("oligo")." An "oligonucleotide" refers to a linear polynucleotide sequence of up to about 100 nucleotide bases in length.

"Open reading frame (ORF)." An "open reading frame" is a series of nucleotide triplets (codons) coding for amino acids without any internal termination codons. These sequences are usually translatable into a peptide.

"Operably linked." A first nucleic acid sequence is "operably linked" with a second nucleic acid sequence when the first nucleic acid sequence is situated in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, are in the same reading frame.

"Orthologs." "Orthologs" are nucleic acid or amino acid sequences that share a common ancestral sequence, but that diverged when a species carrying that ancestral sequence split into two species. Orthologous sequences are usually also homologous sequences.

"Probes and primers." Nucleic acid "probes and primers" readily may be prepared based on the nucleic acid sequences provided by this invention. A "probe" comprises an isolated nucleic acid sequence attached to a detectable label or reporter molecule. These labeled nucleic acid sequences are useful for identifying other promoters and seed-storage proteins. Typical labels include radioactive isotopes, ligands, chemiluminescent agents, and enzymes. Methods for labeling and guidance in the choice of labels appropriate for various purposes are discussed, e.g., in Sambrook et al. (eds.), *Molecular Cloning: A Laboratory Manual*, 2nd ed., vol. 1–3, Cold Spring Harbor Laboratory Press, Cold Spring Harbor, N.Y., 1989; and Ausubel et al. (ed.), *Current Protocols in Molecular Biology*, Greene Publishing and Wiley-Interscience, New York (with periodic updates), 1987.

"Primers" are short nucleic acids, preferably DNA oligonucleotides 15 nucleotides or more in length, that are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in Sambrook et al. (ed.), *Molecular Cloning: A Laboratory Manual*, 2nd ed., vol. 1–3, Cold Spring Harbor Laboratory Press, Cold Spring Harbor, N.Y., 1989; Ausubel et al. (ed.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer™ (Version 0.5, 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target with a higher specificity than a corresponding primer of only 15 nucleotides. Thus, in order to obtain greater specificity, probes and primers may be selected that comprise, by way of example, 10, 20, 25, 30, 35, 40, 50 or more consecutive nucleotides.

"Promoter Activity." "Promoter activity" is defined as the ability of a DNA sequence to drive transcription. Promoter activity varies with the number and position of the promoter elements. For example, the df2SSP promoter can be altered such that it loses its tissue specific-activity (native activity), yet maintains its ability to drive transcription.

"Promoter elements." "Promoter elements" as used herein refers to sub-domains within the promoter that confer tissue-specific expression, enhance expression, or inhibit expression. A promoter can contain a multiplicity of promoter elements. Furthermore, some elements can appear more than once within a single promoter. Examples of such elements are E-box motifs, RY-repeat elements, AT-rich regions, ACGT-core elements, Opaque-2-like elements, and conserved gymnosperm-like regions. Additional examples of promoter elements can be found in U.S. Pat. No.: 5,723,751 to Chua; U.S. Pat. No. 5,608,149 to Barry et al.; U.S. Pat. No. 5,589,615 to De Clercq et al.; U.S. Pat. No. 5,589,583 to Klee et al.; U.S. Pat. No. 5,677,474 to Rogers; U.S. Pat. No. 5,487,991 to Vandekerckhove et al.; and U.S. Pat. No. 5,530,194 to Knauf et al. Typically, a TATA box is found on the 3'-end of the series of promoter elements.

Examples of specific promoter elements are provided above and in the sequence listing. However, one of skill in the art will appreciate that the specific examples shown in the sequence listing can be modified while still maintaining activity. For example a base in an RY-repeat element can be changed without the RY-repeat element losing its functionality within the overall promoter sequence.

Once a promoter has been identified, the promoter elements can be characterized, such as is described below for the Douglas-fir 2S seed-storage promoter (df2SSP). This promoter contains a series of identifiable promoter elements. These elements appear in series in the genomic DNA as is shown schematically in FIG. 2. The space between the elements is hereinafter referred to as "inter-element space." An inter-element space can be modified through the addition, deletion, and/or substitution of nucleotides without the loss of df2SSP biological activity.

The df2SSP promoter (SEQ ID NO: 17) also can be modified by deleting elements from the promoter and/or duplicating elements within the promoter. One of ordinary skill in the art will appreciate that such modifications to the promoter can enhance promoter activity, inhibit promoter activity, or alter the level of tissue-specific expression of the promoter.

One of skill in the art will appreciate that, by modifying the order of the promoter elements, the number of the promoter elements, and/or the length of the inter-element space(s), one can modify native df2SSP promoter activity. However, in each case, the df2SSP promoter will be capable of driving the expression of the gene that is operably linked to it. Assays for quantifying df2SSP activity as well as native df2SSP activity are provided below.

"Protein." A biological molecule expressed by a gene and comprised of amino acids.

"Purified." The term "purified" does not require absolute purity; rather, it is intended as a relative term. Thus, for example, a purified protein preparation is one in which the protein referred to is purer than the protein in its natural environment within a cell or within a production reaction chamber (as appropriate).

"Recombinant." A "recombinant" nucleic acid is one having a sequence that is not naturally occurring or having a sequence made by an artificial combination of two otherwise separated sequences. This artificial combination is often accomplished by chemical synthesis or, more commonly, by the manipulation of isolated segments of nucleic acids, e.g., by genetic engineering techniques.

"Sequence identity." The term "sequence identity" is used to describe the similarity between two nucleic acid sequences or between two amino acid sequences. Sequence identity is typically expressed in terms of percentage identity; the higher the percentage, the more similar the two sequences.

Methods for aligning sequences for comparison purposes are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, Proc. Natl. Acad. Sci. USA 85:2444–2448, 1988; Higgins and Sharp, *Gene* 73:237–244, 1988; Higgins and Sharp, *CABIOS* 5:151–153, 1989; Corpet et al., *Nucl.* Acids Res. 16:10881–10890, 1988; Huang et al., *Comput. Applic. Biosciences* 8:155–165, 1992; and Pearson et al., *Meth. Mol. Biol.* 24:307–331, 1994. Altschul et al., *J. Mol. Biol.* 215:403–410, 1990, presents a detailed discussion of sequence-alignment methods and homology calculations.

The NCBI Basic Local Alignment Search Tool (BLAST™, Altschul et al. *J. Mol. Biol.* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx. BLAST™ can be accessed at the web site maintained by the NCBI. A description of how to determine sequence identity using this program is also available at the web site.

For comparisons of amino acid sequences of greater than about 30 amino acids, the "Blast 2 sequences" function in the BLAST™ program is employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

A first nucleic acid is "substantially similar" to a second nucleic acid if, when optimally aligned (with appropriate nucleotide insertions or deletions) with the other nucleic acid (or its complementary strand), nucleotide-sequence identity occurs in at least about 60%, 75%, 80%, 85%, 90% or 95% of the nucleotide bases. (As used herein, "optimally aligned" sequences exhibit a maximal possible sequence identity). Sequence similarity can be determined by comparing the nucleotide sequences of two nucleic acids using the BLAST™ sequence-analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if it shows sequence identity of at least about 75%–90% or greater when optimally aligned and compared using BLAST™ software (blastp) using default settings.

"Seed-storage protein": A "seed-storage protein" is an endogenous plant protein synthesized and accumulated during seed maturation, stored in the dry seed grain, and mobilized during maturation. Such proteins often are stored in a protein body in a plant seed. Examples of such storage proteins include arachin, avenin, cocosin, conarchin, concocosin, conglutin, conglycinin, convicine, crambin, cruciferin, cucurbitin, edestin, excelesin, gliadin, gluten, glytenin, glycinin, helianthin, hordein, kafirin, legumin, napin, oryzin, pennisetin, phaseolin, psophocarpin, secalin, vicilin, vicine, and zein.

Furthermore, it has previously been shown that seed-storage proteins can be used to enhance and/or alter seed germination (Redenbaugh (ed.), *Synseeds; Application of Synthetic Seeds to Crop Improvement*, CRC Press Inc., 1993). Hence, the disclosure herein of the nucleic acid sequence and amino acid sequence for the 2S seed-storage protein allows for the creation of transgenic plants having altered germination rates.

"Transformed." A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle gun acceleration.

"Transgenic plant." As used herein a "transgenic plant" refers to a plant that contains recombinant genetic material ("transgene") not normally found in a wild-type plant of the same species. Thus, a plant that is grown from a plant cell into which recombinant DNA is introduced by transformation is a transgenic plant, as are all offspring of that plant containing the introduced transgene (whether produced sexually or asexually).

"Vector." A "vector" is a nucleic acid molecule as introduced into a host cell, thereby producing a transformed host cell. A vector may include one or more nucleic acid sequences, such as an origin of replication, that permit the vector to replicate in a host cell. A vector also may include one or more selectable marker genes and other genetic elements known in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

II. Assessment of Promoter Activity

A. Experimental Overview

In order to isolate genes encoding 2S seed-storage proteins, an entire cDNA probe for PM2S1 (Chatthai and Misra, *Planta* 206:138–145, 1998 ) was used to screen a Douglas-fir genomic library. Out of approximately 1×10⁶ plaques screened, a total of six genomic clones were isolated. Of these, a positive lambda clone, λPM2S1-1, which contained an insert of about 20 kilobases, was selected for further analysis. Restriction mapping of the λDNA isolated from the λPM2S1-1 clone was based on Southern analysis using the PM2S1 cDNA probe, which localized the genomic sequence to a 3.5-kb EcoRI fragment. The fragment was subcloned into the pUC19 plasmid, giving rise to a genomic clone gPm2S1 (SEQ ID NO: 10).

B. Characterization Of The gPm2S1 Gene

A 3.5-kb EcoRI region of the recombinant gPm2S1 clone was sequenced to determine the precise organization and structure of a representative gene for a 2S seed-storage protein from Douglas-fir (FIG. 1). Comparison of the gPm2S1 nucleotide sequence (SEQ ID NO: 10) with the PM2S1 cDNA sequence revealed that the transcription unit consisted of two exons separated by an intron. Exon/intron boundaries were assigned based on open-reading-frame discontinuities at each junction and on the colinearity of the gPm2S1 gene (SEQ ID NO: 10) and PM2S1 cDNA on either side of each intron. The plant consensus splice junctions, GT and AG dinucleotides (Brown et al., 1996), were present at 5'- and 3'-ends of the intron, respectively. The intron in the gPm2S1 gene (SEQ ID NO: 10) was located at amino acid position 156. The coding region of the gPm2S1 gene (SEQ ID NO: 10) was not identical to that of the PM2S1 cDNA; however, they shared a high degree of similarity at both the nucleotide level (84%) and the amino acid level (83%). In addition, the 340-bp region downstream of the stop codon (SEQ ID NO: 12) in the gPm2S1 gene (SEQ ID NO: 10) was 70% identical to the 3'-UTR of the PM2S1 cDNA.

A primer-extension assay using total RNA from stage-5 megagametophyte and a 19-mer oligonucleotide (5'PM2S1), complimentary to the 5'-terminus of the PM2S1 coding sequence, was performed to locate the transcription start-site. The longest transcript, as deduced from the sequence ladder produced with the same primer, was initiated from the adenine located 63 nucleotides upstream from the ATG initiation codon. Downstream from the transcription start-site, the ATG initiation codon deduced from the cDNA sequence was the first in-frame ATG codon in the genomic sequence. The sequence CGAAAGAGCAatg (SEQ ID NO: 16) contained only one nucleotide mismatched to the 5'-flanking region of the initiation-start codon of the PM2S1 cDNA. Based on the primer-extension assays, the transcription-start site at the adenine was assigned as the start site and designated as+1.

Comparison of the gPm2S1 gene promoter (SEQ ID NO: 17) with the analogous sequences in genes for 2S seed-storage proteins from angiosperms did not reveal any recognizable similarity. When the promoter sequence of df2SSP promoter sequence (SEQ ID NO: 17) was compared to the promoter sequence of the white spruce Pg2S albumin gene (McInnis et al., *Picea glauca 2S albumin-like seed storage protein (Pg2S) gene, complete coding sequence*. GenBank Accession Number U92077), a low sequence similarity was observed (between 36% to 52%) between the two related genes (FIG. 1).

However, the di2SSP promoter (SEQ ID NO: 17) contains several putative cis-acting elements having sequence similarity to previously described elements. Typical TATA-box (SEQ ID NO: 8) and CAAT-box (SEQ ID NO: 9) sequences are found 30 and 45 base pairs, respectively, upstream of the transcription-initiation site. Repeated occurrence of E-box motifs (7 copies of CANNTG (SEQ ID NO: 1); Kawagoe and Murai, *Plant J*. 2:927–936, 1992) and ACGT-core elements (9 copies (SEQ ID No: 4); Schindler et al., *Plant Cell* 4:1309–1319, 1992) are observed throughout the 1.1kb of 5'-upstream sequence. The RY-repeated element (GCATGC (SEQ ID NO: 2)) responsible for the seed-specific regulation of legumes (Dasgupta et al., *Gene* 133:301–302, 1993) is found at position -112. The sequences TTCGTCATC (SEQ ID NO: 15) and TTTAT-CATC (SEQ ID NO: 16), which are similar to the binding site of opaque-2 transcription factor (TTNNTCATC (SEQ ID NO: 5); Lohmer et al., *EMBO J*. 10:617–624, 1991) are present at about positions -90 and -285. The AT-rich sequence (SEQ ID NO: 3) 29 bp in length, is an example of one such region that extends from position -463 to -492 (i.e. -463 to -492. Other significant regions include AAGATTC-CTCTAA (-180/-192; SEQ ID NO: 6) and GTTGTTGAGA (-229/-238; SEQ ID NO: 7). These latter two sequences appear to be conserved in gymnosperm seed-storage-protein genes such as those encoding *Ginkgo biloba* 11S legumin (Hager et al., *J. Mol. Evol.* 41:457–466, 1995) and white spruce 2S seed-storage proteins (McInnis et al., *Picea glauca 2S albumin-like seed storage protein (Pg2S) gene, complete coding sequence*. GenBank Accession Number U92077).

C. Analysis Of The gPm2S1/uidA Chimeric Gene Activity In Douglas-fir And Transgenic Tobacco In angiosperms, much of the control of seed-storage-protein genes occurs at the level of transcription (Morton et al., *Regulation of Seed Storage Protein Gene Expression*, Kigel and Galili (eds.) Marcel Dekker, Inc., New York, pp. 103–138, 1995). As a first step to identifying the inducible elements, tissue-specific elements, and development-specific elements of the df2SSP promoter (SEQ ID NO: 17), functional studies of the promoter were performed using the uidA (β-glucuronidase (GUS)) gene fused to intact 2S promoter sequences. The GUS-fusion constructs were either assayed in Douglas-fir seeds transformed using particle bombardment or stably introduced into tobacco plants via *Agrobacterium tumefaciens*.

A 1.2-kb gPm2S1(SEQ ID NO: 17)/uidA chimeric gene (p2SSP-1.2) was constructed, and transient expression assays were conducted in seed tissues of Douglas-fir. A GUS construct (pBI101) lacking a promoter served as a negative control, and the constitutive 35S promoter of cauliflower mosaic virus coupled to the GUS gene (pBI221) served as a positive control. The chimeric reporter gene and control constructs were delivered to developing megagametophytes (stage 5) and mid-cotyledonary zygotic embryos (stage 6) by microparticle bombardment, and transient expression of GUS was examined histochemically. The GUS activity was determined as GUS-expression units, evident as blue spots (or in black-and-white images as black spots) on tissue. Bombardments with the reporter gene, pBI101, produced no visible transient GUS expression. By contrast, when the tissues were bombarded with pBI221, GUS activity was evident in both megagametophytes and zygotic embryos. Similarly, the GUS activity was evident when the seed tissues were bombarded with the p2SSP-1.2 gene, showing 23 and 5 GUS expression units per tissue in megagametophyte and zygotic embryo, respectively. The results indicated that the df2SSP promoter (SEQ ID NO: 17) was able to drive expression of the uidA gene in Douglas-fir seeds.

Stable expression studies were carried out using a 1.2-kb gPm2S1(SEQ ID NO:17)/uidA gene fusion (p2SSP121-1.2) that was constructed in a binary vector pBI121, and the chimeric construct was introduced into tobacco via Agrobacterium-mediated transformation. The presence of the chimeric gene integration and the number of uidA gene copies in the transformed tobacco were verified using PCR-amplification and Southern blot analysis, respectively. Staining for GUS activity indicated that the df2SSP promoter (SEQ ID NO: 17) is active in both embryo and endosperm tissue. In embryos, the GUS activity was located in the cotyledons, but not in the embryogenic radicle and root tips. Histochemical staining did not reveal GUS activity in leaves and roots of the transgenic tobacco.

V. Alteration of Promoter Structure

A. Modifications of the Douglas-fir 2S Seed-Storage Protein (df2SSP) Promoter

The structure of a given promoter determines the level of mRNA expression as well as the tissue-specificity of the promoter. However, expression levels and tissue-specificity can be maintained when deletions, substitutions, and/or additions are made to the promoter sequence. Hence, the scope of the invention encompasses df2SSP promoters that have been modified through the incorporation of deletions, substitutions, and/or additions. However, regardless of the number of mutations that are incorporated into the df2SSP promoter, the promoter continues to exhibit df2SSP promoter activity, or native df2SSP promoter activity, as described above.

One possible method of modifying the df2SSP promoter is by inserting additional promoter elements into the promoter sequence. For example, the promoter can be modified such that an E-box motif (SEQ ID NO: 1), RY-repeated element (SEQ ID NO: 2), AT-rich region (SEQ ID NO: 3), ACGT-core element (SEQ ID NO: 4), opaque-2-like binding site (SEQ ID NO: 5), and/or a conserved gymnosperm-like region (SEQ ID NOS: 5 or 6) is added. One of skill in the art will appreciate that standard molecular biology techniques can be used to insert one or more of these elements into the promoter sequence. The modified promoter then can be transiently transfected into gymnosperm, monocot, or dicot tissue and the tissue can be tested for transgene expression.

Similarly, one or more of the existing promoter elements can be deleted from the promoter sequence. The modified promoter can be tested for transcriptional activity and tissue-specificity. Given the disclosure of the df2SSP promoter (SEQ ID NO: 17), it also is possible to make both additions and deletions and test for promoter activity.

Finally, the df2SSP promoter (SEQ ID NO: 17) also can be modified such that the inter-element spaces contain deletions, insertions, and/or substitutions. One of ordinary skill in the art can use standard molecular biology techniques to insert one or more additional nucleic acid residues into the inter-element spaces, delete one or more nucleic acid residues from the inter-element spaces, and/or substitute one or more other sequences into the inter-element spaces. However, regardless of the number and combination of insertions, deletions, and substitutions, the promoter activity or native df2SSP promoter activity (SEQ ID NO: 17) is maintained.

B. Methods Of Producing Douglas-fir 2SSP Promoter, Variants, and Deletion Mutants Thereof 1. Cloning Nucleic Acid Sequences Encoding df2SSP Provided with the nucleic acid sequence of the df2SSP promtoer (SEQ ID NO: 17), one of ordinary skill in the art will appreciate that several different methods can be used to isolate the Douglas-fir df2SSP promoter (SEQ ID NO: 17). One example of such a method is the polymerase chain reaction (PCR) (U.S. Pat. No. 4,683,202 to Mullis; and Saiki et al., Science 239:487–491, 1988). Once isolated, the df2SSP promoter (SEQ ID NO: 17) sequence is useful for driving the expression of transgenes.

When using PCR to isolate a sequence encoding the gene, a first primer can be designed that targets the extreme 5'-end of the sequence, and a second primer can be designed that targets the extreme 3'-end of the sequence. These primers can be used such that they generate multiple copies of the promoter sequence. The copies are isolated by separation on an agarose gel. The fragment of interest then is removed from the gel and ligated into an appropriate vector.

Alternatively, the promoter can be created by engineering synthetic strands of DNA that partially overlap each other (Beaucage and Caruthers, Tetrahedron Lett. 22:1859–1869, 1981; and Matthes et al., Embo. J. 3:801–805, 1984). The synthetic strands are annealed, and a DNA polymerase is used to fill in the single-stranded regions. The resulting synthetic double-stranded DNA molecule can be cloned into a vector.

For use as primers and probes, nucleic acid sequences can contain at least 15, 20, 30, 40, 50, or 60 contiguous nucleic acid residues of the sequence shown in SEQ ID NO: 17 or the complementary strand of the molecule shown in SEQ ID NO: 17. The nucleic acid sequences are useful for performing hybridization protocols, such as Northern blots or Southern blots as described in Sambrook et al., (eds.), Molecular Cloning, A Laboratory Manual, 2d ed., vol. 1–3, Cold Spring Harbor Laboratory Press, Cold Spring Harbor, N.Y., 1989.

These hybridization protocols can be used to identify nucleic acid sequences that are substantially similar to the sequence shown in SEQ ID NO: 17. A successful hybridization to such sequences indicates that the analogous nucleic acid sequence hybridizes to the oligonucleotide probe that comprises at least a fragment of the sequence shown in SEQ ID NO: 17. Generally, hybridization conditions are classified into categories, for example very high stringency, high stringency, and low stringency. The conditions corresponding to these categories for probes of approximately 600 bp are provided below.

Very High Stringency (detects sequences that share 90% sequence identity)

| Hybridization in 5x | SSC at 65° C. | 16 hours |
| Wash twice in 2x | SSC at room temp. | 15 minutes each |
| Wash twice in 0.2x | SSC at 65° C. | 20 minutes each |

High Stringency (detects sequences that share 80% sequence identity or greater)

| Hybridization in 3x | SSC at 65° C. | 16 hours |
| Wash twice in 2x | SSC at room temp. | 15 minutes each |
| Wash twice in 0.5x | SSC at 55° C. | 20 minutes each |

Low Stringency (detects sequences that share greater than 50% sequence identity)

| Hybridization in 3x | SSC at 65° C. | 16 hours |
| Wash twice in 2x | SSC at room temp. | 20 minutes each |

Variant df2SSP-promoter (SEQ ID NO: 17) sequences may be produced by standard DNA-mutagenesis techniques, for example, M13 primer mutagenesis. Details of these techniques are provided in Sambrook et al. (ed.), Molecular Cloning: A Laboratory Manual, 2nd ed., vol. 1–3, Ch. 15, Cold Spring Harbor Laboratory Press, Cold Spring Harbor, N.Y., 1989; and Ausubel et al. (ed.) *Current Protocols in Molecular Biology*, Greene Publishing and Wiley-Interscience, New York (with periodic updates), 1987. By the use of such techniques, variants may be created that differ slightly from the df2SSP promoter sequences specifically disclosed, yet that still encode a promoter having promoter activity. DNA molecules and nucleotide sequences that are derivatives of those specifically disclosed herein and that differ from those disclosed by the deletion, addition, or substitution of nucleotides while still maintaining promoter activity and/or native df2SSP promoter activity are comprehended by this invention.

2. Transformation

The DNA constructs of the invention, containing the df2SSP promoter (SEQ ID NO: 17) operably linked to one or more transgenes may be either homologous or heterologous to the host in question. If homologous to the host cell, i.e., the transgene is produced by the host cell in nature, the construct may be connected operably to another secretory signal sequence and/or terminator sequence than in the natural environment. In this context, the term "homologous" is intended to include a cDNA sequence encoding a transgene that is native to the host cell. The term "heterologous" is intended to include a transgene not expressed by the host cell in nature. Thus, the DNA sequence may be from another organism, or it may be a synthetic sequence.

The host cell of the invention, into which the DNA construct or the recombinant expression vector of the invention is to be introduced, may be any cell capable of driving expression of the df2SSP promoter (SEQ ID NO: 17). Such cells include bacteria cells, yeast cells, fungal cells, insect cells, plant cells, and other higher eukaryotic cells.

Various methods of introducing the DNA construct into host cells are well known in the art. For example, in some species, the Ti plasmid of *A. tumefaciens* can be used to transform host cells (Gouka et al., *Nature Biotech.* 6:598–602, 1999). The host cell also can be transformed using gene blasting techniques (described above) and standard chemical treatments.

V. Examples

The following non-limiting examples are provided to illustrate particular features of the present invention. The scope of the present invention should not be limited to those features exemplified.

A. Douglas-fir Genomic DNA Preparation

Spring-flush needles of Douglas-fir were used for isolation of high-molecular-weight genomic DNA according to De Verno et al., *Information Report. Petawawa National Forestry Institute, Canadian Forestry Service*. PI-X-88, 1989, with some modifications. Fifty grams of needles were surface-sterilized, ground to a fine powder in liquid nitrogen and mixed with 400 mL of cold extraction buffer (50 mM Tris-HCl pH 8.0, 5 mM EDTA, 0.35 M sorbitol, 0.1% BSA, 10% PEG, 0.1% spermine, 0.1% spermidine, and 0.1% β-mercaptoethanol). The mixture was filtered through cheese cloth and miracloth. The pellet was recovered by centrifugation at 9000 rpm for 15 min and resuspended in 50 mL of wash buffer (50 mM Tris-HCl pH 8.0, 25 mM EDTA, 0.35 M sorbitol, 0.1% β-mercaptoethanol). The solution was mixed with 10 mL of 5% sarcosyl, 7 mL of 5M NaCl and 5 mL of 8.6% cetyltrimethylammonium bromide (CTAB) in 0.7 M NaCl and incubated at 60° C. for 15 min. The mixture was extracted with chloroform:isoamyl alcohol (24:1, v/v). The DNA was precipitated with 2 volumes of cold ethanol and collected by centrifiugation. The DNA pellet was washed with 70% cold ethanol and gently dissolved in TE buffer.

B. Construction Of A Douglas-fir Genomic Library

A Douglas-fir genomic library was constructed according to the protocol for the lambda EMBL3/BamHI vector kit (Stratagene, La Jolla, Calif.). Briefly, Douglas-fir genomic DNA was isolated from spring-flush needles as described above, and purified by ultracentrifugation through a CsCl gradient (Sambrook et al. (ed.), *Molecular Cloning: A Laboratory Manual*, 2nd ed., vol. 1–3, Ch. 15, Cold Spring Harbor Laboratory Press, Cold Spring Harbor, N.Y., 1989). The DNA was partially digested with Sau3AI, and DNA fragments ranging from 9 to 20 kb were purified from a 0.7% low-melting-point agarose gel. The size-selected DNA fragments were treated with calf intestine alkaline phosphatase (CIAP), ligated into BamHI half-site arms of λEMBL3 according to the manufacturer's instructions (Stratagene), and packaged in vitro into phage particles using the Gigapack® II packaging system (Stratagene). A titer for the stored Douglas-fir genomic library was $6 \times 10^{10}$ pfu/mL.

C. Screening Of The Douglas-fir Genomic Library

The Douglas-fir genomic DNA library was plated with *E. coli* XL1-Blue MRA cells (600 μL of $OD_{600}$=0.5 in 10 mM $MgSO_4$) on NZY plates at approximately $5 \times 10^4$ pfu per 150×15 mm plate. Plaque lifting, membrane preparation, prehybridization, hybridization, and membrane washing were performed as described in the cDNA library screening, except that radiolabeled PM2S1 and PM2.1 cDNA inserts were used as probes to isolate Douglas-fir 2S seed-storage protein and metallothionein-like protein genes, respectively. After the secondary screening, recombinant genomic lambda clones were amplified, and stored as phage stocks at 4° C.

D. DNA Sequence Analysis

DNA sequences were determined from both strands by the dideoxynucleotide chain termination method using Sequenase™ version 2.0 (United States Biochemical, Cleveland, Ohio). Commercially available and custom-synthesized primers were used.

For each reaction, 5 μg of plasmid DNA were denatured by adding 0.1 volume of a mixture of 2 M NaOH and 2 mM EDTA, and incubating 30 min at 37° C. The solution was neutralized by adding 0.1 volume of 3 M sodium acetate pH 5.2. The DNA was precipitated with 2 volumes of ethanol at −80° C. for 30 min. After centrifugation, the pelleted DNA was washed with 70% ethanol, and stored at −20° C. until further use. Annealing of the primer to the DNA template was performed in 10 μL (40 mM Tris-HCl pH 7.5, 20 mM $MgCl_2$, 50 mM NaCl, 10% DMSO, 1 pmol primer) at 37° C. for 30 min. After annealing, 3 μM each of dGTP, dCTP and dTTP, 10 mM DTT, 5 μCi of ($\alpha$-$^{35}$S) dATP (1000 Ci/mmol, DuPont), and 1 unit of Sequenase™ version 2 T7 DNA polymerase were added. The mixture was incubated for 2–5 min at room temperature. Aliquots of 3.5 μL of the mixture were added to four tubes containing 2.5 μL of the respective termination reaction (G, A, T or C), each containing 80 μM of each dGTP, dATP, dTTP and dCTP, 50 mM NaCl, and 8 μM of either ddGTP, ddATP, ddTTP or ddGTP. The four tubes were incubated at 37° C. for 5 min. The reactions were stopped with 4 μL of stop solution (95% formamide, 20 mM EDTA, 0.5% bromophenol blue, and 0.5% xylene cyanol). The sequencing reaction was heated at 80° C. for 2 min, and 2.5 μL of each reaction were loaded on a sequencing gel (6% acrylamide/bis-acrylamide (19:1, w/w), 7 M urea, 1X glycerol tolerance gel buffer, 1% ammonium persulfate, 0.025% TEMED). Electrophoresis was performed at 50 watts in glycerol tolerance gel buffer (0.1 M Tris, 30 mM taurine, 0.5 mM EDTA). After electrophoresis, the gel was transferred to Whatman 3MM paper (Whatman International Ltd., Maidstone, England) and vacuum-dried for 2 h at 80° C. The gel was exposed to X-Omat™ film (Eastman Kodak Co., Rochester, N.Y.) at room temperature overnight to 3 days.

E. Plant Transformation

Immature seeds of what corresponding to early- and mid-cotyledonary stages were collected. The seeds were surface-sterilized in 1% sodium hypochlorite for 5 min and rinsed 3 times in sterilized water before megagametophytes and zygotic embryos were separated. Aseptically germinated 4-week-old seedlings were used as the source of needles and roots. All samples were placed on BM-3 medium (Gupta and Pullman, U.S. Pat. No. 5,036,007) in a 60-mm diameter Petri dish and used for particle bombardment.

F. Construction Of Gus Expression Vectors

For construction of the p2SSP 1.2 clone, an approximately 1.16-kb fragment of the 5'-flanking sequence of the gPm2S1 gene was PCR amplified from the plasmid gPm2S1-EK1.3 using a pair of primers containing HindIII and XbaI recognition sites at the 5'-end and 3'-end of the promoter fragment, respectively. The PCR product was cloned between the HindIII and XbaI sites of pBI 221, replacing the CaMV 35S promoter. The resulting clone contained approximately 1.16 Kb of the 5' planting sequence of the gPM251 gene upstream from the GUS-coding sequence.

G. Particle Bombardment

Particle bombardment was performed with the PDS-1000/He Particle Delivery System (Bio-Rad Laboratories, Richmond, Calif.) according to the instructions provided by the manufacturer. DNA was precipitated onto gold particles (1.5–3.0 μm diameter; Aldrich Chemicals) as described by Klein et al., *Proc. Natl. Acad. Sci USA* 85:4305–4309, 1988. A gold-suspension (60 mg/mL) was prepared in 50% glycerol. Fifty microliters of the suspension were aliquoted into a microcentrifuge tube to which 8 μg of promoter-GUS plasmid DNA, 50 μL of 2.5 M $CaCl_2$, and 20 μL of 0.1 M spermidine were added. All additions were made by continuously vortexing the tube. The gold particles were allowed to settle, and pelleted by a brief centrifugation. The supernatant was discarded, 140 μL cold 70% ethanol and 140 μL cold absolute ethanol were added without disturbing the pellets, and the liquid phase was immediately removed. DNA-coated gold particles were resuspended in 100 μL absolute ethanol, and aliquots of 10 μL (0.8 μg DNA associated with 0.3 mg of gold particles) were delivered to respective macrocarrier disks and air-dried. The following parameters were used for each bombardment: the gap distance between the rupture membrane and the disk was 0.6 cm, the disk traveled 1.6 cm before impacting with a steel stopping screen, and target tissues were placed 6.0 cm from the stopping screen and bombarded once at 1300 or 1550 psi. The sample chamber was evacuated to 20 inches of mercury and the gas-acceleration tube was pressurized with the selected helium gas pressure. Each experiment was repeated three to four times, on different days, with freshly prepared new batches of DNA-coated gold particles. The reported data are means of the results obtained from these repeats.

H. Tobacco Transformation

The pBI121-recombinant plasmids were transferred from *E. coli* DH5α cells into *Agrobacterium tumefaciens*. Young leaves of Nicotiana tabacum cv. Xanthi were surface-sterilized in 1% (v/v) sodium hypochlorite for 2–5 min. and rinsed well with sterile water. Leaf discs were co-cultivated with the overnight-cultured *A. tumefaciens*, transferred onto Murashige and Skoog (MS) medium, and incubated for 2 days at 25° C. The co-cultivated leaf discs were transferred to a shoot-inducing medium (MS medium containing 0.01 μg/mL NAA, 2.0 μg/mL 6-BA, 100 μg/mL kanamycin, and 200 μg/mL carbenicillin). Young shoots were transferred to a root-inducing medium (MS medium containing 100 μg/mL kanamycin and 200 μg/mL carbenicillin). Regenerated plants were tested for the presence of chimeric gene constructs using PCR-amplification of genomic DNA. The transgenic tobacco plants were transferred to soil and developing seeds were collected.

I. Histochemical Assay For Gus Transient Expression

Bombarded explants remained on the same plates for 24–48 h before they were subjected to GUS assay (Jefferson et al., *EMBO J.* 6:3901–3907, 1987). The tissues were immersed in 500 μL of X-gluc staining solution (2 mM X-gluc, 50 mM sodium phosphate buffer pH 7.0, 10 mM EDTA, 0.5 mM potassium ferricyanide, 0.5 mM potassium ferrocyanide, 0.1% Triton X-100) overnight at 37° C. The number of blue spots were counted and photographed under a stereo dissecting microscope.

Having illustrated and described the principles of the invention in multiple embodiments and examples, it should be apparent to those skilled in the art that the invention can be modified in arrangement and detail without departing from such principles. Therefore, the invention includes all modifications coming within the spirit and scope of the following claims.

What is claimed is:

1. A recombinant promoter comprising SEQ ID NO: 17, wherein the promoter is capable of driving expression of a transgene operably linked to the recombinant promoter.

2. A vector, comprising a recombinant promoter as recited in claim 1.

3. A host cell, comprising a vector as recited in claim 2.

4. A transgenic plant, comprising a host cell as recited in claim 3.

5. A transgene, comprising a promoter as recited in claim 1 and at least one ORF operably linked to the promoter.

6. A vector, comprising a transgene as recited in claim 5.

7. A plant cell, comprising a vector as recited in claim 6.

8. The transgene of claim 5, wherein the ORF encodes a cationic peptide.

9. The plant cell of claim 7, wherein the plant cell is obtained from a plant selected from the group consisting of a maize, a wheat, a rice, a millet, a tobacco, a sorghum, a rye, a barley, a brassica, a seaweed, a lemna, an oat, a soybean, a legume, a rape/canola, an alfalfa, a cotton, a flax, a peanut, a clover, a cucurbits, a cassava, a potato, a vegetable, a citrus tree, a fruit tree, a flower, a deciduous tree, a conifer, a turf grass, a cacao, a rubber tree and a member of the genus Hevea.

10. A method for expressing at least one protein in a host cell, comprising:
    introducing the transgene of claim 6 into a host cell; and
    allowing the host cell to produce a protein from the ORF.

11. The method of claim 10, wherein the host cell is a plant host cell.

12. The method of claim 10, wherein the protein is a cationic peptide.

13. The promoter of claim 1, wherein the promoter is tissue-specific.

14. The promoter of claim 13, wherein the promoter drives gene expression in seed tissue.

15. A recombinant promoter comprising at least 8 promoter elements, the elements being selected from the group consisting of E-box motifs (SEQ ID NO: 1), RY-repeat elements (SEQ ID NO: 2), AT-rich regions (SEQ ID NO: 3), ACGT-core elements (SEQ ID NO: 4), opaque-2-like elements (SEQ ID NO: 5), gymnosperm-like regions (SEQ ID NOs: 6 and 7), and duplicates thereof, wherein at least one of the 8 promoter elements is the RY-repeat element (SEQ ID NO: 2), and wherein the promoter displays promoter activity.

16. The recombinant promoter of claim 15, wherein the promoter comprises at least 10 promoter elements.

17. The recombinant promoter of claim 15, comprising, in order: 3'-E-box motif (SEQ ID NO: 1); ACGT-core element (SEQ ID NO: 4); E-box motif (SEQ ID NO: 1); E-box motif (SEQ ID NO: 1); E-box motif (SEQ ID NO: 1); E-box motif (SEQ ID NO: 1); ACGT-core element (SEQ ID NO: 4); ACGT-core element (SEQ ID NO: 4); ACGT-core element (SEQ ID NO: 4); AT-rich region (SEQ ID NO: 3); ACGT-core element (SEQ ID NO: 4); ACGT-core element (SEQ ID NO: 4); gymnosperm-like region (SEQ. ID NOs: 6 or 7); ACGT-core element (SEQ ID NO: 4); E-box motif (SEQ ID NO: 1); opaque-2-like element (SEQ ID NO: 5); gymnosperm-like region (SEQ. ID NOs: 6 or 7); ACGT-core element (SEQ ID NO: 4); opaque-2-like element (SEQ ID NO: 5); gymnosperm-like region (SEQ ID NOs: 6 or 7); ACGT-core element (SEQ ID NO: 4); RY-repeat element (SEQ ID NO: 2); E-box motif (SEQ ID NO: 1); and opaque-2-like element (SEQ ID NO: 5)-5'.

18. A transgene, comprising the promoter of claim 15 operably linked to an ORF.

19. A host cell, comprising the transgene of claim 18.

20. A transgenic plant, comprising the transgene of claim 18.

21. The transgenic plant of claim 20, wherein the plant is a maize, a wheat, a rice, a millet, a tobacco, a sorghum, a rye, a barley, a seaweed, a lemna, an oat, a soybean, a legume, a rape/canola, an alfalfa, a brassica, a cotton, a flax, a peanut, a clover, a cucurbits, a cassava, a vegetable, a citrus tree, a fruit tree, a flower, a deciduous tree, a conifer, a turf grass, a cacao, a rubber tree or a member of the genus Hevea.

22. The transgene according to claim 18, wherein the ORF encodes a cationic peptide.

23. The recombinant promoter of claim 15, wherein the promoter comprises at least 12 promoter elements.

24. The recombinant promoter of claim 15, wherein the promoter comprises at least 14 promoter elements.

25. The recombinant promoter of claim 15, wherein the promoter comprises at least 16 promoter elements.

26. The recombinant promoter of claim 15, wherein one of the 8 promoter elements is the AT-rich region (SEQ ID NO: 3).

27. The recombinant promoter of claim 15, wherein one of the 8 promoter elements is the ACGT-core element (SEQ ID NO: 4).

28. The recombinant promoter of claim 15, wherein one of the 8 promoter elements is the opaque-2-like element (SEQ ID NO: 5).

29. The recombinant promoter of claim 15, wherein one of the 8 promoter elements is the gymnosperm-like regions (SEQ ID NOs: 6 and 7).

* * * * *

UNITED STATES PATENT AND TRADEMARK OFFICE
CERTIFICATE OF CORRECTION

PATENT NO. : 6,541,222 B1 Page 1 of 1
DATED : April 1, 2003
INVENTOR(S) : Santosh Misra It is certified that error appears in the above-identified patent and that said Letters Patent is hereby corrected as shown below:

<u>Colunm 4,</u>
Line 46, "4 gymnosperm-like" should be -- gymnosperm-like --.

Signed and Sealed this

Fourteenth Day of October, 2003

JAMES E. ROGAN
*Director of the United States Patent and Trademark Office*

SEQUENCE LISTING

<160> NUMBER OF SEQ ID NOS: 18

<210> SEQ ID NO 1
<211> LENGTH: 6
<212> TYPE: DNA
<213> ORGANISM: Pseudotsuga menziesii
<220> FEATURE:
<221> NAME/KEY: variation
<222> LOCATION: (3)..(4)
<223> OTHER INFORMATION: N = A, C, G, or T

<400> SEQUENCE: 1 canntg                                                              6

<210> SEQ ID NO 2

```
<211> LENGTH: 6
<212> TYPE: DNA
<213> ORGANISM: Pseudotsuga menziesii

<400> SEQUENCE: 2 gcatgc                                                                     6

<210> SEQ ID NO 3
<211> LENGTH: 29
<212> TYPE: DNA
<213> ORGANISM: Pseudotsuga menziesii

<400> SEQUENCE: 3
aaaaattaat atttaatgtt aatattaat                                           29

<210> SEQ ID NO 4
<211> LENGTH: 4
<212> TYPE: DNA
<213> ORGANISM: Pseudotsuga menziesii

<400> SEQUENCE: 4 acgt                                                                       4

<210> SEQ ID NO 5
<211> LENGTH: 9
<212> TYPE: DNA
<213> ORGANISM: Pseudotsuga menziesii
<220> FEATURE:
<221> NAME/KEY: variation
<222> LOCATION: (3)..(4)
<223> OTHER INFORMATION: N = A, C, G, and T

<400> SEQUENCE: 5 ttnntcatc                                                                  9

<210> SEQ ID NO 6
<211> LENGTH: 13
<212> TYPE: DNA
<213> ORGANISM: Pseudotsuga menziesii

<400> SEQUENCE: 6
aagattcctc taa                                                            13

<210> SEQ ID NO 7
<211> LENGTH: 10
<212> TYPE: DNA
<213> ORGANISM: Pseudotsuga menziesii

<400> SEQUENCE: 7
gttgttgaga                                                                10

<210> SEQ ID NO 8
<211> LENGTH: 4
<212> TYPE: DNA
<213> ORGANISM: Pseudotsuga menziesii

<400> SEQUENCE: 8 tata                                                                       4

<210> SEQ ID NO 9
<211> LENGTH: 4
<212> TYPE: DNA
<213> ORGANISM: Pseudotsuga menziesii

<400> SEQUENCE: 9
```

<210> SEQ ID NO 10
<211> LENGTH: 2419
<212> TYPE: DNA
<213> ORGANISM: Pseudotsuga menziesii

<400> SEQUENCE: 10

```
gaattcgtac tctgctttgt atcgagttat tgtgtttttg ttttacacgt ggcagggatc    60
ttgtttgtta tttctatgca cttagtcact actgtaattt ggttaagaat tttaattcag   120
atgcagttaa agatgaagag catatctagt tgaaaaacta tgagcttaac tagcttcgga   180
ggcagagcta aagtagttag gacagaagta aaaacatcat aaatagaaat agagcatgta   240
gctttgttag atctaacatc aaaccataa acaacagggt tagtttacct tatttctcaa    300
gtgcaaaggc aggaacatat ccataggttc caaatgcata gtttggagca gtggttccag   360
atttcgacaa agcatatcta catcctatag attaagttga actggcaaca taagtgacag   420
catatctaca tctggtaggc tatggcatca acggtggtgt gtcttatcaa gggtcatcca   480
ccttgtgaaa gggtgtgaca tgcattaaca aagtcctacc atcaaattgt gaaatgcatt   540
atgcatcaga taggtggcac catcatgttt caagtaagta agatagtgtt gtgaagtggt   600
gattccctca taccagacta gaaaaattaa tatttaatgt taatattaat gttagcatta   660
ttgaacttca taatctctta gtgaactaag tgggttatgt ctgggttatt tcttgagatt   720
acgtcgttcc caatagaagt gttgttgcgt taaaccttgc cgatgaaaac aacgtgaaac   780
atctacacca ccttacgaaa aatggcatta cgagaagagg aaggcagttt atcatcacct   840
aattagtttg tctaaatgca ataagcctaa gtagtgttgt tgagacgcta gactgcactg   900
tcgcggattc cacatgcccg caagattcct ctaatcgaaa gacgcggcga ttggaaatag   960
aggtaggctt tctttctcag cgtggaatcc gaattggggc atgctttaca tgtgttcgtt  1020
tcgtcatcgt ctgtattcta cgtccctaca gcatacagac accttcaatt cccgggcttt  1080
tataaatacc cacttactct tcccaacttc acactcgcgc ttcatctatc aatccatcat  1140
tcattgtaac gaagaaagaa cagcgaaaga gcaatgggtg tttttttcccc ttcgacaacg  1200
aagctgacgc ttaaatggct gagtgtaggc gtggcgcttc tccttctcct tcactggggt  1260
acccccgacg ttgacgcgca tgaacacaat atatatggag aaaattcgca acagcaacag  1320
caacgacgcg ggtcgtgcga tccggagaga ttgtcttctt gccggactg cttggagcgg  1380
cggagagagc agccatcgga gagttgctgc aacgaattgg aaagaatgtc tccacaatgc  1440
cgatgcccag ccatacagca agtgctcgat caatctgcat cgaccttcat ggattctgac  1500
gatgcactta atcaacgccg tgggccgcga agggcaggtc gaagagaaga gcaggagatg  1560
gcggagagag cccgatacct tccagataca tgcaacgtcc aggagcctcc ccgccgctgc  1620
gatattcgac gcccctctcg taagtctctc ccagttacta attaatagaa tatcgcccct  1680
ctcgtaagtc tctcccagtt actaattaat agacaaatag taactaattt gggtagctgt  1740
tttagtaggg agctgcggtc cagcgtttta agtatgatgt ggttaagcac attatttcat  1800
gttaatgcta tctattttaa tacattctat agtccaccat tttcgttgac ataatttaca  1860
tatatgtaag cacttcccct gcctgccata atgaatgatg aaattaattt atgtactggt  1920
tgtgggtgta caggctattc cataaggggc gtcagttttt gagtgacgaa caagaagaga  1980
atatagatac tatgtagata aataaacgag gggagcactt caaaccgcta tgaatttgtg  2040
```

```
gttttcgttt tcgttttgga ggagcttatt atagttatat atctataggc tctcatctaa    2100
tttcatttga cgcccagcgc ttgtatcata gccggatcta ttccctggta tgtaataaag    2160
aactgaatga atgagaaaat tgatttcatg gtaggatctc ttttcttctt ttcttcggtt    2220
tcatctaatg ggcgccactt acttcatagc aggaccactt ctcttatatg taataaagca    2280
ataaagcact gaatgaacga gcaaactcaa gtttcagagt aaagagtaga agtagactca    2340
ttaagtatct taaaatgtcc aacttcgcat acatcacaac tagcagctca aattttgaa     2400 tgattatcaa ttgccgagt                                                 2419

<210> SEQ ID NO 11
<211> LENGTH: 789
<212> TYPE: DNA
<213> ORGANISM: Pseudotsuga menziesii

<400> SEQUENCE: 11
atgggtgttt tttccccttc gacaacgaag ctgacgctta aatggctgag tgtaggcgtg     60
gcgcttctcc ttctccttca ctggggtacc cccgacgttg acgcgcatga acacaatata    120
tatggagaaa attcgcaaca gcaacagcaa cgacgcgggt cgtgcgatcc ggagagattg    180
tcttcttgcc gggactactt ggagcggcgg agagagcagc catcggagag ttgctgcaac    240
gaattggaaa gaatgtctcc acaatgccga tgcccagcca tacagcaagt gctcgatcaa    300
tctgcatcga ccttcatgga ttctgacgat gcacttaatc aacgccgtgg gccgcgaagg    360
gcaggtcgaa gagaagagca ggagatggcg gagagagccc gataccttcc agatacatgc    420
aacgtccagg agcctccccg ccgctgcgat attcgacgcc cctctcgtaa gtctctccca    480
gttactaatt aatagaatat cgcccctctc gtaagtctct cccagttact aattaataga    540
caaatagtaa ctaatttggg tagctgtttt agtagggagc tgcggtccag cgttttaagt    600
atgatgtggt taagcacatt atttcatgtt aatgctatct attttaatac attctatagt    660
ccaccatttt cgttgacata atttacatat atgtaagcac ttcccttgcc tgccataatg    720
aatgatgaaa ttaatttatg tactggttgt gggtgtacag gctattccat aaggggcgtc    780
agttttttga                                                          789

<210> SEQ ID NO 12
<211> LENGTH: 340
<212> TYPE: DNA
<213> ORGANISM: Pseudotsuga menziesii

<400> SEQUENCE: 12
gtgacgaaca agaagagaat atagatacta tgtagataaa taaacgaggg gagcacttca     60
aaccgctatg aatttgtggt tttcgttttc gttttggagg agcttattat agttatatat    120
ctataggctc tcatctaatt tcatttgacg cccagcgctt gtatcatagc cggatctatt    180
ccctggtatg taataaagaa ctgaatgaat gagaaaattg atttcatggt aggatctctt    240
ttcttctttt cttcggtttc atctaatggg cgccacttac ttcatagcag gaccacttct    300
cttatatgta ataaagcaat aaagcactga atgaacgagc                          340

<210> SEQ ID NO 13
<211> LENGTH: 164
<212> TYPE: PRT
<213> ORGANISM: Pseudotsuga menziesii

<400> SEQUENCE: 13
```

```
Met Gly Val Phe Ser Pro Ser Thr Thr Lys Leu Thr Leu Lys Trp Leu
 1               5                  10                  15

Ser Val Gly Val Ala Leu Leu Leu Leu His Trp Gly Thr Pro Asp
             20                  25                  30

Val Asp Ala His Glu His Asn Ile Tyr Gly Glu Asn Ser Gln Gln Gln
             35                  40                  45

Gln Gln Arg Arg Gly Ser Cys Asp Pro Glu Arg Leu Ser Ser Cys Arg
     50                  55                  60

Asp Tyr Leu Glu Arg Arg Glu Gln Pro Ser Glu Ser Cys Cys Asn
 65                  70                  75                  80

Glu Leu Glu Arg Met Ser Pro Gln Cys Arg Cys Pro Ala Ile Gln Gln
                 85                  90                  95

Val Leu Asp Gln Ser Ala Ser Thr Phe Met Asp Ser Asp Ala Leu
             100                 105                 110

Asn Gln Arg Arg Gly Pro Arg Arg Ala Gly Arg Arg Glu Glu Gln Glu
         115                 120                 125

Met Ala Glu Arg Ala Arg Tyr Leu Pro Asp Thr Cys Asn Val Gln Glu
     130                 135                 140

Pro Pro Arg Arg Cys Asp Ile Arg Arg Pro Ser Arg Tyr Ser Ile Arg
145                 150                 155                 160

Gly Val Ser Phe

<210> SEQ ID NO 14
<211> LENGTH: 9
<212> TYPE: DNA
<213> ORGANISM: Pseudotsuga menziesii

<400> SEQUENCE: 14 ttcgtcatc                                                                9

<210> SEQ ID NO 15
<211> LENGTH: 9
<212> TYPE: DNA
<213> ORGANISM: Pseudotsuga menziesii

<400> SEQUENCE: 15 tttatcatc                                                                9

<210> SEQ ID NO 16
<211> LENGTH: 13
<212> TYPE: DNA
<213> ORGANISM: Pseudotsuga menziesii

<400> SEQUENCE: 16
cgaaagagca atg                                                          13

<210> SEQ ID NO 17
<211> LENGTH: 1111
<212> TYPE: DNA
<213> ORGANISM: Pseudotsuga menziesii

<400> SEQUENCE: 17
gaattcgtac tctgctttgt atcgagttat tgtgtttttg ttttacacgt ggcagggatc        60
ttgtttgtta tttctatgca cttagtcact actgtaattt ggttaagaat tttaattcag       120
atgcagttaa agatgaagag catatctagt tgaaaaacta tgagcttaac tagcttcgga       180
ggcagagcta aagtagttag gacagaagta aaaacatcat aaatagaaat agagcatgta       240
gctttgttag atctaacatc aaaaccataa acaacagggt tagtttacct tatttctcaa       300
```

```
gtgcaaaggc aggaacatat ccataggttc caaatgcata gtttggagca gtggttccag      360
atttcgacaa agcatatcta catcctatag attaagttga actggcaaca taagtgacag      420
catatctaca tctggtaggc tatggcatca acggtggtgt gtcttatcaa gggtcatcca      480
ccttgtgaaa gggtgtgaca tgcattaaca aagtcctacc atcaaattgt gaaatgcatt      540
atgcatcaga taggtggcac catcatgttt caagtaagta agatagtgtt gtgaagtggt      600
gattccctca taccagacta gaaaaattaa tatttaatgt taatattaat gttagcatta      660
ttgaacttca taatctctta gtgaactaag tgggttatgt ctgggttatt tcttgagatt      720
acgtcgttcc caatagaagt gttgttgcgt taaaccttgc cgatgaaaac aacgtgaaac      780
atctacacca ccttacgaaa aatggcatta cgagaagagg aaggcagttt atcatcacct      840
aattagtttg tctaaatgca ataagcctaa gtagtgttgt tgagacgcta gactgcactg      900
tcgcggattc cacatgcccg caagattcct ctaatcgaaa gacgcggcga ttggaaatag      960
aggtaggctt tctttctcag cgtggaatcc gaattggggc atgctttaca tgtgttcgtt     1020
tcgtcatcgt ctgtattcta cgtccctaca gcatacagac accttcaatt cccgggcttt     1080
tataaatacc cacttactct tcccaacttc a                                    1111
```

<210> SEQ ID NO 18
<211> LENGTH: 5
<212> TYPE: DNA
<213> ORGANISM: Artificial Sequence
<220> FEATURE:
<223> OTHER INFORMATION: Description of Artificial Sequence: Binding
      site

<400> SEQUENCE: 18 tgacg                                                                    5